(12) United States Patent
Bauer et al.

(10) Patent No.: US 6,231,529 B1
(45) Date of Patent: May 15, 2001

(54) ELECTROACOUSTIC TRANSDUCER

(75) Inventors: Edgar Bauer, Kraichtal; Werner Krauss, Knittlingen, both of (DE)

(73) Assignee: Richard Wolf GmbH, Knittlingen (DE)

(*) Notice: Subject to any disclaimer, the term of this patent is extended or adjusted under 35 U.S.C. 154(b) by 0 days.

(21) Appl. No.: 09/105,785

(22) Filed: Jun. 26, 1998

(30) Foreign Application Priority Data

Jan. 8, 1997 (DE) .............................. 197 33 233

(51) Int. Cl.$^7$ ............................................. A61B 17/22
(52) U.S. Cl. .................. 601/4; 600/459; 367/157
(58) Field of Search .................. 601/2–4; 600/437, 600/439, 459; 606/2–5; 310/369; 367/151, 153, 155, 157

(56) References Cited

U.S. PATENT DOCUMENTS

| | | |
|---|---|---|
| 3,202,736 | 8/1965 | Horan et al. . |
| 4,087,716 | 5/1978 | Heywang . |
| 4,127,749 * | 11/1978 | Atoji et al. . |
| 4,186,323 * | 1/1980 | Cragg et al. . |
| 4,618,796 * | 10/1986 | Reidlinger . |
| 4,865,042 * | 9/1989 | Umemura et al. ............... 128/660.03 |
| 5,101,133 | 3/1992 | Schäfer . |
| 5,163,436 * | 11/1992 | Saitoh et al. ..................... 128/662.03 |
| 5,193,527 * | 3/1993 | Schaffer ................................ 128/24 |
| 5,488,951 * | 2/1996 | Bauer et al. ...................... 128/653.1 |
| 5,549,110 | 8/1996 | Krauss et al. . |
| 5,762,066 * | 6/1998 | Law et al. ....................... 128/660.03 |
| 5,805,726 * | 9/1998 | Yang et al. . |
| 5,941,838 * | 8/1999 | Eizenhofer . |

FOREIGN PATENT DOCUMENTS

| | | |
|---|---|---|
| 3425992 A1 | 1/1986 | (DE) . |
| 34 25 922 C2 | 10/1986 | (DE) . |
| 31 19 295 C2 | 5/1987 | (DE) . |
| 0 462 311 A1 | 12/1991 | (EP) . |

* cited by examiner

Primary Examiner—Marvin M. Lateef
Assistant Examiner—Shawna J. Shaw
(74) Attorney, Agent, or Firm—Akin, Gump, Strauss, Hauer & Feld, L.L.P.

(57) ABSTRACT

The electroacoustic transucer comprises a dome-shaped carrier on whose inner side are mounted piezoelctric elements and which furthermore is also provided with piezoelectric elements on its outer side. The piezoelectric elements on the inner and on the outer side are switched in separate groups and can be triggered such that the sound waves produced by them can be synchronized, by which means the power intensity in the focus can be increased.

12 Claims, 5 Drawing Sheets

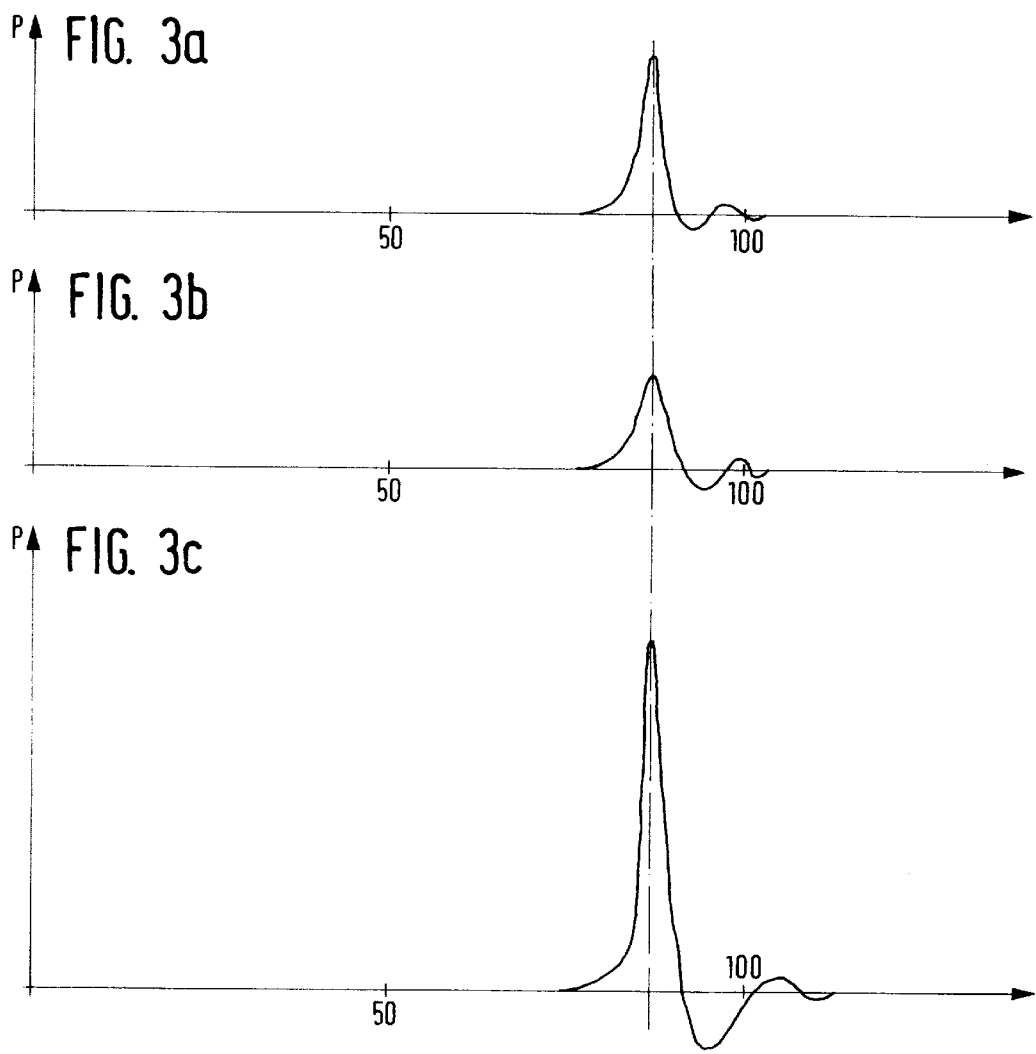

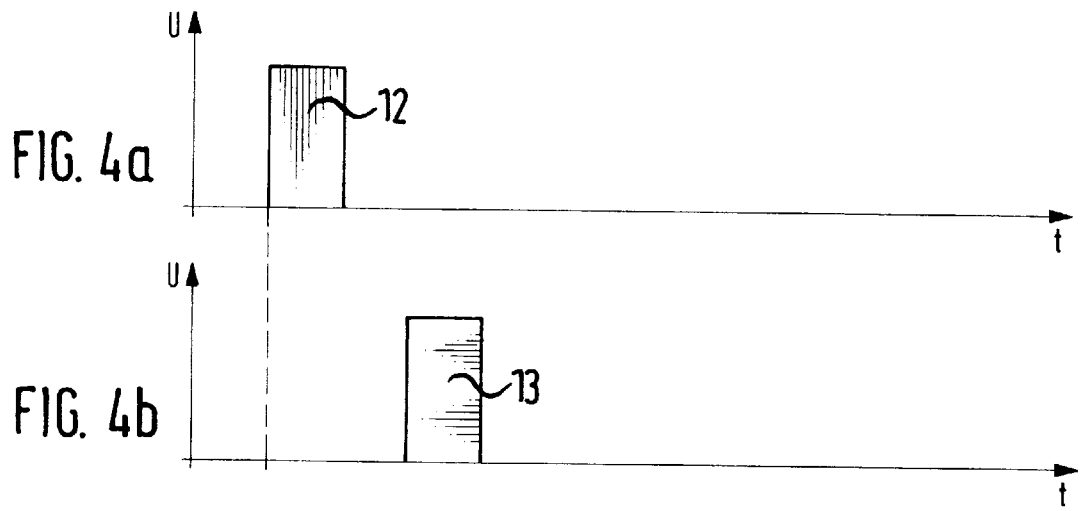
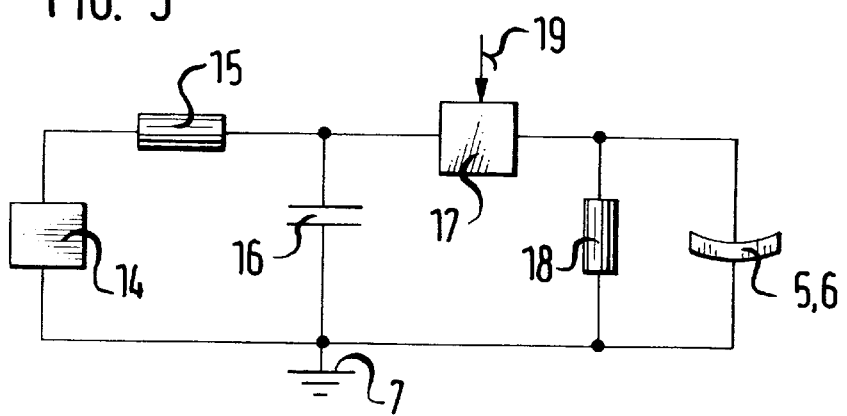

ELECTROACOUSTIC TRANSDUCER

BACKGROUND OF THE INVENTION

The invention relates to an electroacoustic transducer with the features specified in the introductory part of claim 1. Electroacoustic transducers of this type consist of a dome-shaped carrier which on its inner side is furnished with piezoelectric elements which in each case are electrically contacted on a side directed to the carrier as well as a side distant from the carrier and connected to a high voltage impulse generator. On applying a voltage by way of the piezoelectric effect a sound wave in the form of a pressure wave is produced, which on account of the dome-shaped arrangements of the piezoelectric elements is focussed to a point or a region which is dependent on the radius of curvature of the carrier. With such electroacoustic transducers, apparatus for medical treatment, for example lithotripters are equipped whose regions of applications are numerous (from the destruction of stones to the treatment of soft tissue and pain).

An advantage of these piezoelectric transducers with a dome-shaped carriers and piezoelectric elements arranged thereon lies in the high energy intensity in the focus region which can hardly be reached by other systems, by which means a directed and largely pain-free application of shock waves may be effected. The complete irradiated sound power however on account of the limited available irradiation surface may not be increased further beyond certain limits. An enlargement of the irradiating surface can specifically only be achieved by enlarging the radius of the dome or by enlarging the opening angle (aperture). The first is in practise not possible since with this the constructional size of the sound source would increase so much that the application in the field of table apparatus would no longer be possible. An enlargement of the aperture angle can likewise be ruled out since otherwise the penetration depth of the shock waves in the patient itself would become so slight and any increase in power would be compensated by this.

On the other hand one strives rather to reduce in size the constructional shape of the transducer in order to reduce the constructional size of the therapy apparatus and thus to form new fields of application, for example treatment of salival stones or treatment of pain. The acoustic power of the transducer may be increased by electrically precharging the piezoeclectric elements but this increase in power is at the expense of the life expectancy of the transducer dome.

From DE 31 19 295 it is known to arrange several electrical transducers behind one another and to so trigger these in a delayed manner that their pressure waves add. Such an arrangement has been found to be unsuitable with the application of piezoelectric transducer domes, since the focus region in the direction of the treatment depth is heavily extended which is undesirable. Furthermore it has been found out that enormous losses are caused by damping which the sound waves undergo when they must penetrate through a prior-mounted transducer. Finally also these inner friction losses are at the expense of the life expectancy, in particular of the foreward transducer dome directed towards the treatment location.

BRIEF SUMMARY OF THE INVENTION

Against this state of the art it is the object of the present invention to design an electroacoustic transducer of the previously mention constructional type such that the effective sound power irradiated to the therapy loaction is increased without significantly increasing the constructional size or reducing the life expectancy.

According to the invention this object is achieved by those feature specified in claim 1.

Surprisingly it has been shown that an increase in power may be achieved by comparatively simple measures if a dome-shaped carrier on its inner and outer side is provided with piezoelectric elements. With this the damping effect occuring by way of the connecting behind one another of several electroacoustic transducers practically does not occur since the piezoelectric elements on the outer side as well as on the inner side are seated the same carrier and thus acoustic coupling losses by intermediate layers practically do not occur. Furthermore the constructional size by way of this compact arrangement of elements on the front and rear side of the carrier may be kept relatively small.

Preferably the carrier is designed of metal, for example an aluminium or brass dome so that it may not only assume a carrying function for the piezoelectric elements, but at the same time also an electrical function for these. For this purpose the piezoelectric elements are conductingly connected with the carrier, for example by adhesing by way of a conducting, e.g. silver-containing epoxy adhesive. If the piezoelectric elements, which is useful, are formed essentially in a cylindrical shape, with one end face they may be fastened on the carrier and a multitude of elements may be arranged next to one another.

Amazingly it has been found out that for reasons of manufacturing technology as well as for power reasons it is useful to arrange the piezoelectric elements of the outer and inner side not axially equal in pairs but to arrange them essentially randomly on the carrrier in order to be able thus to mount a higher number of piezoelectric elements and thus to obtain a higher sound power. The arrangement of the piezoelectric elements thus is effected exclusively from the point of view of the highest packing density.

If the metallic carrier is connected to a pole of the piezoelectric elements, then this should be switched to the minus pole and the carrier contacted to earth. Then on the one hand the carrier dome by way of a lateral flange or other projection may serve at the same time the mechanical fixation within the apparatus and the electrical safety against the application of electrical high voltage impulses to the apparatus may be reliably secured in a simple manner by way of earthing the apparatus.

In order to electrically insulate the piezoelectric elements laterally to one another it is useful to arrange these with a lateral distance to one another. An inner connection of these is achieved in that these intermediate spaces are filled with a high voltage stable insulating casting mass, so that an acoustic quasi-homogeneous layer is formed.

In order to further optimize the sound power of the transducer, on the rear side of the transducer, thus on the side of the outer-side piezoelectric elements which is distant to the carrier, a backing as a reflection body may be provided. Such a reflection body may be formed as a metal body, which will achieve a high degree of reflection, but also may be formed of a suitable plastic of compound material. In order to ensure a good acoustic coupling of the reflection body to the piezoelectric elements, the reflection body is preferably connected to the piezoelectric elements of the outer side by a casting mass. It is also conceivable instead of a separate reflection body to form the casting mass itself as such, for this for example metal chips may be added to the casting mass.

Usefully the electrical connection of the piezoelectric elements is effected in two groups in a manner such that the piezoelectric elements located on the inner side can be separately electrically triggered. Then specifically by way of a directed temporal triggering of the impulses, running time differences of the acoustic waves between the outside and inside groups may be compensated for or produced in a directed manner, in order to increase the sound intensity in the focus region or to expand the focus region.

In order to achieve this it is useful to allocate to the electrical transducer two generators, able to be triggered independently of one another, for producing high voltage impulses, more specifically a generator for the inside group and a generator for the outside group of piezoelectric elements. Also when the generators function independently of one another, they should however be tunable with one another in a manner such that the directed superposition of the sound waves of both groups of piezoelectric elements is possible.

BRIEF DESCRIPTION OF THE DRAWINGS

The invention is hereinafter described in more detail by way of embodiment examples shown in the drawings. There are shown.

DETAILED DESCRIPTION OF THE INVENTION

Figure 1:
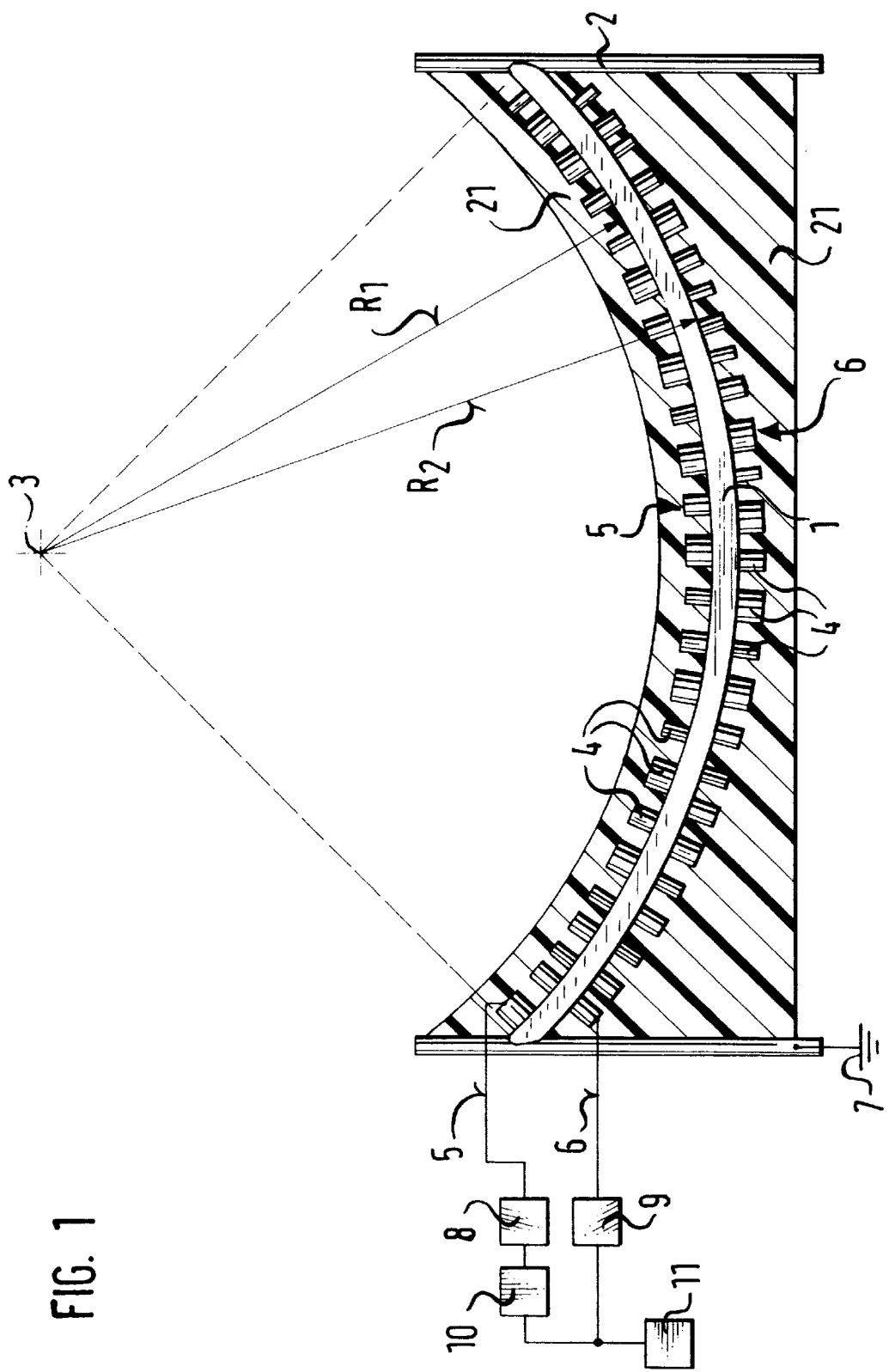
FIG. 1 in a schematic representation a longitudinal section through a transducer according to the invention, FIG. 2 the pressure course in the focus with simultaneous impulse application to both groups of piezoelectric transducers, FIG. 3 the pressure course in the focus with the directed triggering of the impulse application, FIG. 4 the electrical signal for application to both groups, FIG. 5 the construction of a high voltage impulse generator and FIG. 6 a further embodiment form of a transducer according to the invention in the representation according to FIG. 1.

The transducer represented by way of FIG. 1 consists of a carrier 1 in the form of an aluminium dome, which is designed as one-piece with a tube section 2, with which the transducer is fixed to the apparatus arrangement, e.g. a therapy apparatus. The dome-shaped carrier 1 comprises on its inner side facing the focus 3 a radius $R_1$ and on its outer side distant to this a radius $R_2$. The radii $R_1$ and $R_2$ proceed from a common centre point, specifically the focus 3 of the electroacoustic transducer. On its inner side as well as on the outer side the carrier is furnished with a multitude of piezoelectric elements 4 which comprise an essentially cylindrical shape and are arranged at a lateral distance to one another essentially randomly and according to the principle of the highest packing density. The piezoelectric elements 4 are respectively fastened with one of their end faces to the inner or outer side of the carrier 1 and are conductingly connected to this. With the represented embodiment form the elements 4 are electrically conductingly fastened with a conducting silver-containing epoxy adhesive to the front or rear side of the carrier dome 1. The free end faces of the piezoelectric elements 4 are contacted by way of thin silvered copper wires which here are fastened in an electrically conducting manner and with a material fit by way of a soldering point (not represented). The intermediate spaces of the front side and rear side piezoelectric elements 4 are filled out with the high-voltage-stable insulating material 21 which also encloses the elements at their free end faces and which is formed dome-shaped towards the focus, whilst to the rear side it comprises a level flat ending (see FIG. 1). As a casting mass epoxy or polyurethane casting material is applied.

The triggering of the piezoelectric elements 4 is effected in the manner known per se by way of high voltage impulses, wherein however the elements arranged on the inside of the carrier 1 are amalgamated with regard to the switching to an (inner) group 5 and the piezoelectric elements arranged on the outer side of the carrier 1 to an (outer) group 6, these able to be triggered separately from one another.

For reasons of safety the carrier 1 continuously forms the minus pole of both groups 5 and 6 of piezoelectric elements 4 and is always at zero potential by way of the earth connection 7.

Each of the groups 5 and 6 of piezoelectric elements 4 is triggered via its own high voltage impulse generator 8 and 9 respectively. Connected prior to one of the two high voltage impulse generators—in the embodiment example represented by FIG. 1 the high voltage impulse generator 8—is a time function element 10 (delay). Both high voltage impulse generators may be triggered independently from one another and are triggered by a trigger module 11. This switching permits the high voltage impulses for the groups 5 and 6 of piezoelectric elements 4 to be delivered synchronously or with an adjustable temporal delay to one another. Also a switching of only the front or only the rear group 5, 6 is possible.

Figure 2A:
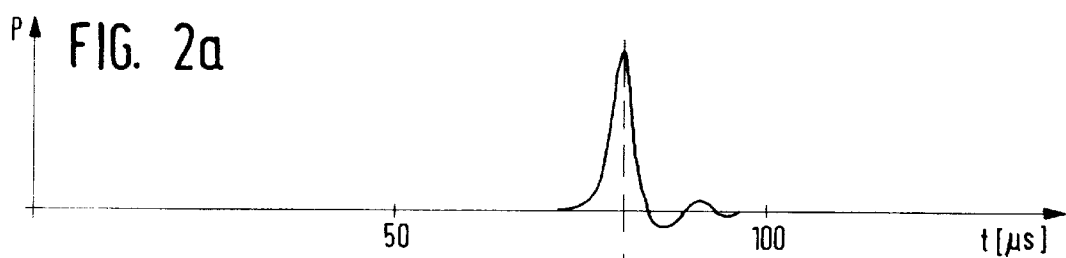
Figure 2B:
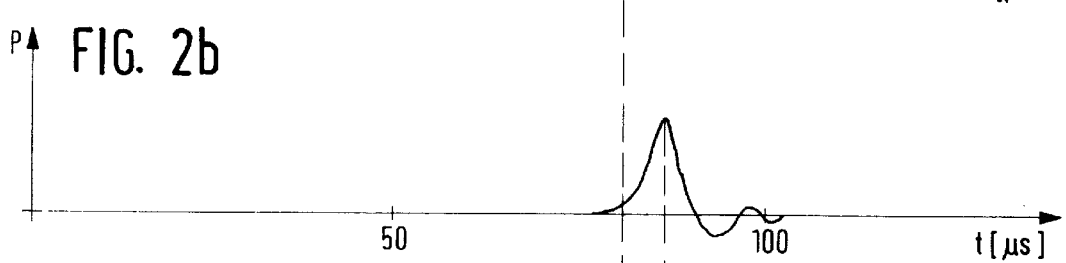
Figure 2C:
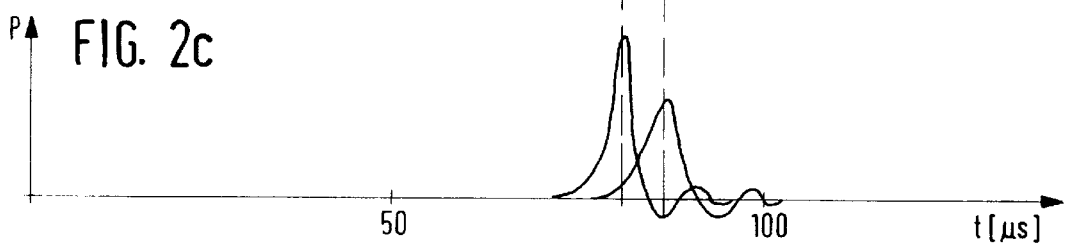

By way of FIG. 2 the course of pressure in the focus 3 is represented, wherein FIG. 2a shows the pressure course after application of a high voltage impulse to the inner group 5, FIG. 2b the pressure course after application of a high voltage impulse to the outer group 6 and FIG. 2c the pressure course after simultaneous application of a high voltage impulse to both groups 5 and 6. It can be clearly recognized that the pressure wave resulting from the high voltage impulse to the outer group 6 is flatter in its course and delayed with respect to that of the inner group 5. The smaller amplitude is due to the increased damping losses whilst the delay is due to the longer running time which the sound waves produced by the outer group 6 have to the focus. These must specifically pass through a greater distance $R_2$ with respect to the inner group 5. From this there results the pressure course, of two pressure waves directly following one another, which is shown in FIG. 2c given the synchronous high voltage impulse application to both groups 5 and 6.

By way of the time function element 10 a time delayed high voltage impulse application to the inner group 5 with respect to the outer group 6 may be effected in a manner such that the pressure waves produced by both groups run synchronously, as is represented by way of FIG. 3c. The FIGS. 3a and 3b represent the pressure course in the focus 3 which results when respectively only the inner group 5 or only the outer group 6 is applied with a high voltage impulse, wherein the running time differences are already compensated for. As FIG. 3c makes clear, with a suitable temporal adaptation not only an addition of the pressure waves produced by the outer group 6 and by the inner group 5 is effected, but furthermore a steepening by which means an enormous increase in power is effect with respect to conventional electroacoustic transducers. Apart from this extremely high energy intensity represented by way of FIG. 3c, by way of a suitable alteration of the time function element 10 the steepness of the produced pressure impulse may be set in an almost unlimited manner. Also the power of the transducer may be reduced in almost unlimited manner by way of triggering only the inner group 5 or also only the outer group 6. This electroacoustic transducer thus has a very high dynamic range which further permits a setting of the focus region by way of a suitable electrical triggering. Minimal energy concentrations are for example achieved when only the outer group 6 of piezoelectric elements 4 are triggered, since then the non-active piezoelectric elements 4 of the inner group 5 form a damping layer.

In FIG. 4 it is represented which temporal sequence the high voltage impulses 12, 13 (idealized representation as rectangular impulses) must have so that a maximum steepening of the pressure wave in the focus 3 according to FIG. 3c is effected. The high voltage rectangular impulse shown in FIG. 4a for the outer group 6 of piezoelectric elements is produced several $\mu$-seconds before the high voltage impulse 13 according to FIG. 4b provided for the inner group 5 of piezoelectric elements 4. The time difference corresponds to the running time difference of the sound waves to the focus.

By way of FIG. 5 the construction of the high voltage impulse generator 8, 9 is shown. The high voltage impulse generator comprises a high voltage charging apparatus 14 which via a resistance 15 is connected to a high voltage capacitor 16. The high voltage capacitor 16 is charged by the high voltage charging apparatus 14 via the charging resistance 15. Via a high voltage switch 17 this high voltage capacitor 16 is connected to a group 5 or 6 of parallel connected piezoelectric elements 4 as well as to a discharging resistance 18 connected parallel thereto. The high voltage switch 17 comprises a trigger input 19 and is formed as a semiconductor switch, e.g. high voltage transistor or high voltage thyristor in order to be able to exactly execute switching procedures in the $\mu$-second range.

Figure 6:
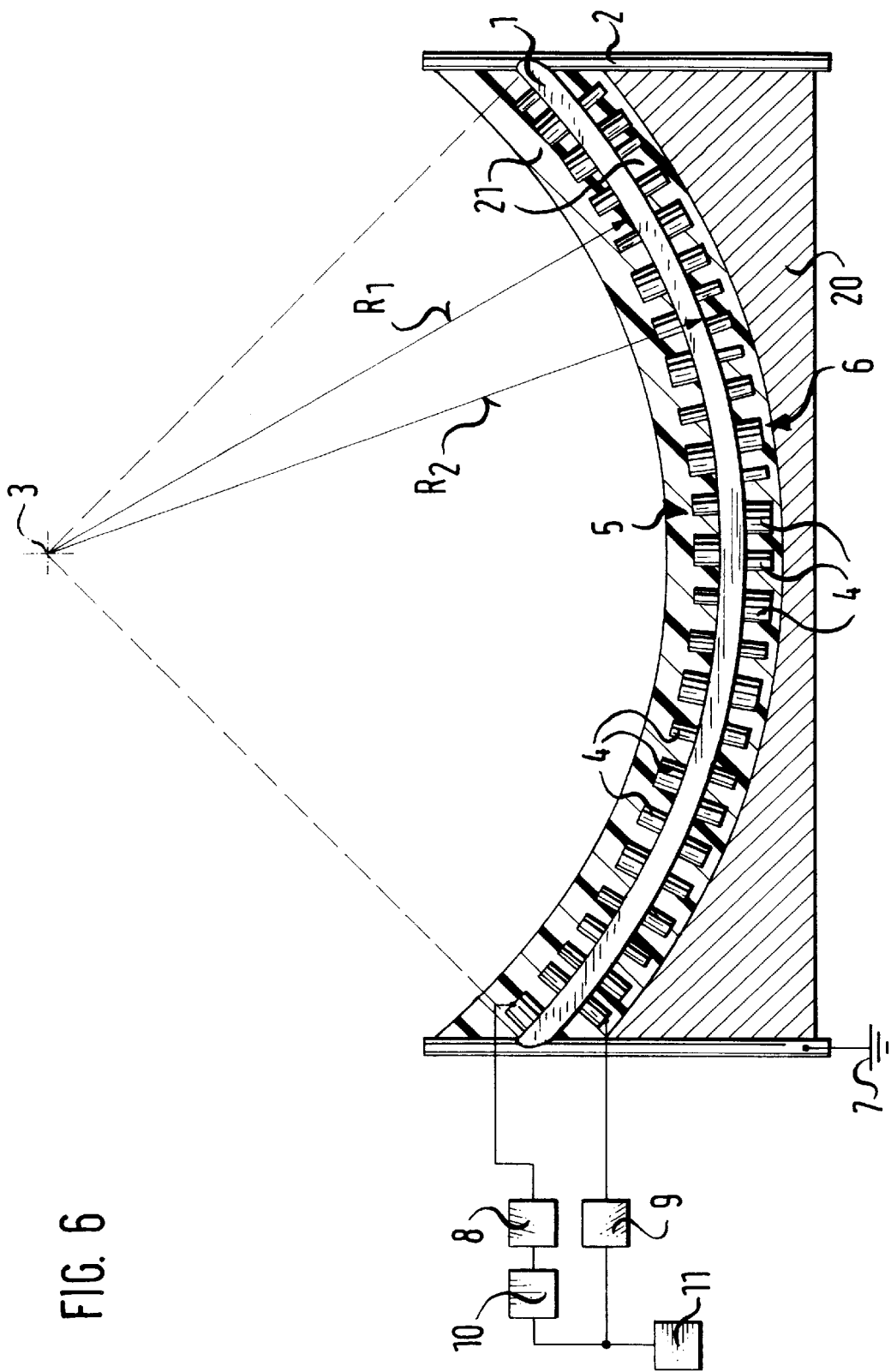

FIG. 6 shows an embodiment variation, which differs from that according to FIG. 1 in that the outer group 6 of piezoelectric elements 4 also in the rearward end face region is only provided with a thin layer of casting mass 21, and here is provided with a reflection body 20 which is acoustically coupled to the piezoelectric elements 4 via a casting mass and is formed dome-shaped towards the focus 3, wherein the centre point of the dome coincides with the focus 3. The reflection body 20 consists of metal, in the present embodiment of aluminium, but however may also be formed by an undirect casting, for example in the form of an epoxy resin enriched with metal particles. The reflection body 20 increases the efficiency in particular of the outer group 6 of piezoelectric elements 4.

What is claimed is:

1. An electroacoustic transducer comprising a dome-shaped carrier and a plurality of piezoelectric elements mounted on an inner side and an outer side of the carrier.

2. The electroacoustic transducer according to claim 1, wherein the carrier is comprised of a metal and the piezoelectric elements are connected to the carrier in a conducting manner.

3. The electroacoustic transducer according to claim 1, wherein the piezoelectric elements have essentially a cylindrical shape and bear with one end face on the carrier.

4. The electroacoustic transducer according to claim 1, wherein the piezoelectric elements on the inner side and the outer side of the carrier are arranged essentially randomly according to the principle of highest packing density.

5. The electroacoustic transducer according to claim 1, wherein the carrier is grounded.

6. The electroacoustic transducer according to claim 1, wherein the piezoelectric elements are arranged at a lateral distance to one another and the intermediate spaces between the piezoelectric elements are filled out with a high-voltage-stable insulating casting mass.

7. The electroacoustic transducer according to claim 1, wherein the piezoelectric elements provided on the outer side of the carrier are provided with a reflection body on the outer side of the carrier.

8. The electroacoustic transducer according to claim 7, wherein the reflection body is formed by a common metal body which by way of a casting mass is acoustically coupled to the piezoelectric elements on the outer side of the carrier.

9. The electroacoustic transducer according to claim 7, wherein the reflection body is formed by a casting mass which covers the piezoelectric elements on the outer side of the carrier.

10. The electroacoustic transducer according to claim 1, wherein the piezoelectric elements on the outer side of the carrier and the piezoelectric elements on the inner side of the carrier can be electrically triggered separately.

11. The electroacoustic transducer according to claim 1, further comprising a first generator and a second generator which may be triggered separately from one another, for producing high voltage impulses, wherein the first generator is allocated to the piezoelectric elements on the inner side of the carrier and the second generator is allocated to the piezoelectric elements on the outer side of the carrier.

12. The electroacoustic transducer according to claim 11, wherein the first and second generator can be triggered for the directed superposition of the sound waves produced by the piezoelectric elements on the outer side of the carrier and the piezoelectric elements on the inner side of the carrier.

* * * * *